United States Patent [19]

Franz et al.

[11] 4,254,046

[45] Mar. 3, 1981

[54] METHOD FOR MAKING DIMETHYLTIN DIFLUORIDE

[75] Inventors: Helmut Franz, Pittsburgh; Paul F. Duffer, Creighton; James H. Hanlon, Pittsburgh, all of Pa.

[73] Assignee: PPG Industries, Inc., Pittsburgh, Pa.

[21] Appl. No.: 9,016

[22] Filed: Feb. 5, 1979

[51] Int. Cl.³ .............................................. C07F 7/22
[52] U.S. Cl. ................................................ 260/429.7
[58] Field of Search ...................................... 260/429.7

[56] References Cited

U.S. PATENT DOCUMENTS

| | | | |
|---|---|---|---|
| 3,493,592 | 2/1970 | Shapiro et al. | 260/429.7 |
| 3,661,958 | 5/1972 | Onozuka et al. | 260/429.7 |
| 3,857,868 | 12/1974 | Witman et al. | 260/429.7 |

OTHER PUBLICATIONS

Malner, ACTA Pharm. Jugoslav 18 3, 117 (1968).
Hobbs et al., Inorg. Chem. 9 1037 (1970).
Lewchuk et al., Inorg. Chem. 11 43 (1972).
Krause, Ber 51, pp. 1447-1456 (1918).
J. Organometal. Chem. 17, p. 153 (1969).

*Primary Examiner*—Helen M. S. Sneed
*Attorney, Agent, or Firm*—Donna L. Seidel

[57] ABSTRACT

A method is disclosed for making dimethyltin difluoride by reacting dimethyltin dichloride with an alkali metal or ammonium fluoride salt.

6 Claims, No Drawings

METHOD FOR MAKING DIMETHYLTIN DIFLUORIDE

FIELD OF THE INVENTION

The present invention relates generally to the art of synthesizing dimethyltin difluoride and more particularly to the art of making dimethyltin difluoride from dimethyltin dichloride.

THE PRIOR ART

Hobbs and Tobias disclose reacting dimethyltin oxide with aqueous hydrofluoric acid to form dimethyltin difluoride in *Inorganic Chemistry*, 9, 1037 (1970). The preparation of dimethyltin difluoride by reacting dimethyltin dichloride with aqueous hydrofluoric acid is disclosed by Lewchuck et al in *Inorganic Chemistry*, 11, 43 (1972).

SUMMARY OF THE INVENTION

The present invention involves the conversion of dimethyltin dichloride to dimethyltin difluoride using simple alkali metal or ammonium fluoride salts in aqueous solution. Dimethyltin dichloride and an alkali metal or ammonium fluoride salt are reacted in aqueous solution resulting in the precipitation of dimethyltin difluoride.

DESCRIPTION OF THE PREFERRED EMBODIMENT

A solution of neutral alkali metal or ammonium fluoride salt is prepared. Preferred salts include potassium fluoride, ammonium fluoride and ammonium bifluoride. The solution may be maintained at ambient temperature or heated to a temperature up to the boiling point of the solution. Preferably, the solution is either maintained at ambient temperature for simplicity or heated to a temperature between about 100° and 200° F. (about 38° to 93° C.), preferably 100° to 140° F. (about 38° to 60° C.), for efficiency.

The aqueous fluoride solution is added to dimethyltin dichloride which may be in solid form but is, preferably an aqueous solution comprising about 50 percent by weight dimethyltin dichloride at ambient or elevated temperature. As the reaction between the fluoride and dimethyltin dichloride proceeds, dimethyltin difluoride precipitates form the aqueous reaction medium. The precipitate is collected, preferably by filtration, and preferably washed and dried.

The dimethyltin difluoride thus produced is useful as a coating reactant for the preparation of tin oxide films. The present invention will be further understood by the descriptions of specific examples which follow.

EXAMPLE I 1000 grams of ammonium bifluoride, $NH_4F \cdot HF$, is dissolved in approximately one liter of water at ambient temperature. This solution is added to 2500 milliliters of dimethyltin dichloride solution. The solution, available as Methyltin Chloride 8020 from Cincinnati Milacron, is about 50 percent by weight solids which typically comprise about 80 percent dimethyltin dichloride and 20 percent monomethyltin trichloride. Dimethyltin difluoride, identified by infrared spectroscopy and quantitative elemental analysis, begins to precipitate instantly. Allowing the reaction to proceed for about an hour optimizes the yield.

EXAMPLE II

Ammonium bifluoride solution is added to dimethyltin dichloride solution as in Example I except that the solution temperature is maintained between 100° and 140° F. (about 38° to 60° C.). Optimum yield of dimethyltin difluoride is obtained in about 10° to 15° minutes.

EXAMPLE III

An aqueous solution of ammonium fluoride, $NH_4F$, is added to a dimethyltin dichloride solution as in Example I. Dimethyltin difluoride begins to precipitate from the reaction medium immediately.

EXAMPLE IV

An aqueous solution of potassium fluoride, $KF \cdot 2H_2O$ is added to a dimethyltin dichloride solution as in Example I. Dimethyltin difluoride immediately precipitates from the reaction solution.

The above examples are offered to illustrate the present invention, the scope of which is defined by the following claims.

We claim:

1. A method for making dimethyltin difluoride comprising the steps of:
   a. selecting a source of fluoride from the group consisting of alkali metal fluoride, ammonium fluoride and ammonium bifluoride;
   b. preparing an aqueous solution of the selected fluoride; and
   c. reacting dimethyltin dichloride with said fluoride in essentially aqueous solution to precipitate dimethyltin difluoride.

2. The method according to claim 1, which further comprises the step of recovering the precipitated dimethyltin difluoride from the aqueous solution.

3. The method according to claim 1, wherein an aqueous solution of the fluoride is added to an aqueous solution of dimethyltin dichloride.

4. The method according to claim 1, wherein solid dimethyltin dichloride is added to an aqueous solution of the fluoride.

5. The method according to claim 1, wherein the reaction is conducted at a temperature between 100° and 200° F. (about 38° to 93° C.).

6. The method according to claim 5, wherein the reaction is conducted at a temperature between 100° and 140° F. (about 38° to 60° C.).

* * * * *